(12) United States Patent
Suzuki

(10) Patent No.: US 7,954,949 B2
(45) Date of Patent: Jun. 7, 2011

(54) HAND-HELD OCULAR FUNDUS IMAGING APPARATUS

(75) Inventor: Takayoshi Suzuki, Hamamatsu (JP)

(73) Assignee: Kowa Company Ltd. (JP)

( * ) Notice: Subject to any disclaimer, the term of this patent is extended or adjusted under 35 U.S.C. 154(b) by 461 days.

(21) Appl. No.: 11/810,769

(22) Filed: Jun. 7, 2007

(65) Prior Publication Data

US 2007/0291225 A1 Dec. 20, 2007

(30) Foreign Application Priority Data

Jun. 20, 2006 (JP) .................................. 2006-169497

(51) Int. Cl.
*A61B 3/10* (2006.01)
(52) U.S. Cl. ........................ 351/218; 351/206; 351/221
(58) Field of Classification Search .................. 351/218, 351/206, 221, 205, 200, 246
See application file for complete search history.

(56) References Cited

U.S. PATENT DOCUMENTS

| | | | |
|---|---|---|---|
| 2,195,169 A | 2/1940 | Graff | 88/20 |
| 3,586,424 A * | 6/1971 | Schenk et al. | 351/213 |
| 4,715,703 A | 12/1987 | Cornsweet et al. | 351/205 |
| 5,629,747 A * | 5/1997 | Miyake | 351/218 |
| 6,350,031 B1 | 2/2002 | Lashkari et al. | 351/221 |

FOREIGN PATENT DOCUMENTS

| | | |
|---|---|---|
| DE | 1949236 | 1/1971 |
| GB | 995529 | 6/1965 |
| GB | 2353868 | 3/2001 |
| WO | 02096279 | 12/2002 |

* cited by examiner

*Primary Examiner* — Hung X Dang
(74) *Attorney, Agent, or Firm* — Adams & Wilks

(57) ABSTRACT

A lightweight and compact hand-held ocular fundus imaging apparatus is provided wherein alignment can be easily performed while ensuring a working length. An examiner takes hold of a grip by hand and secures a face pad against part of the face of a patient. The examiner performs alignment by tilting a reflecting mirror, and when alignment is complete, an image of the fundus of the patient's eye is taken. An optical system except for the reflecting mirror is disposed on the inside of a main body portion that includes the grip and the face pad, and the reflecting mirror is disposed on the outside of the main body portion. A lever for tilting the reflecting mirror is disposed on the grip. With this type of configuration, the alignment operation can be performed easily and reliably by moving the reflecting mirror while maintaining the apparatus main body in a stable state.

24 Claims, 4 Drawing Sheets

HAND-HELD OCULAR FUNDUS IMAGING APPARATUS

BACKGROUND OF THE INVENTION

1. Field of the Invention

The present invention relates to a hand-held ocular fundus imaging apparatus, and specifically to a hand-held ocular fundus imaging apparatus wherein an examiner takes hold of a grip by hand and secures a face pad or the hand holding the grip against part of a patient's face to form an fundus image of the patient's eye.

2. Description of the Prior Art

In conventional practice, there have been small hand-held fundus cameras wherein an examiner takes hold of a grip by hand and secures the apparatus against part of a patient's face to photograph the fundus (Japanese Laid-open Patent Application Nos. 2005-143805 and 1992-256726).

Examples of known fundus cameras include a fundus camera wherein illuminating light is directed onto the fundus via a reflecting mirror disposed in the optical path of a photographic aperture and a cornea, and alignment is performed by varying the angle of the reflecting mirror (Japanese Laid-open Patent Application No. 2002-345758). A fundus camera is also known in which alignment is performed by moving slit light with the aid of a mirror in two dimensions to illuminate the fundus (Japanese Laid-open Patent Application Nos. 1994-7301 and 1981-83326).

The conventional hand-held fundus cameras have problems in that since the positional relationship with the patient's eye is not stable, it is difficult to align the photographic optical system with the patient's eye, i.e., to perform an alignment operation. In order to reduce the size of the fundus camera to make it light in weight, the working distance becomes as short as 10 mm or less. Since the main body is still heavy and alignment is difficult, it is not easy to operate the apparatus comfortably, and since the working distance is short, the distal end of the fundus camera is highly likely to come into contact with the cornea of the patient's eye, thus creating constant danger.

The present invention was devised in order to resolve such problems, and an object thereof is to provide a hand-held ocular fundus imaging apparatus that is lightweight and compact and is capable of performing alignment easily while ensuring a working distance.

SUMMARY OF THE INVENTION

The present invention provides a hand-held ocular fundus imaging apparatus operated while a face pad or a hand holding a grip is secured against part of a patient's face. The apparatus comprises a tiltable reflecting mirror for moving the position of an entrance pupil, and an optical system for observing and photographing a patient's eye via the reflecting mirror, wherein the reflecting mirror is tilted to perform positional alignment relative to the patient's eye.

The present invention also provides a hand-held ocular fundus imaging apparatus wherein a face pad or a hand holding a grip is secured against part of a patient's face to image a fundus of a patient's eye. The apparatus comprises a tiltable reflecting mirror for moving the position of an entrance pupil, and an optical system for observing and photographing a patient's eye via the tiltable reflecting mirror. The optical system except for the reflecting mirror is disposed inside a main body portion containing the grip, and the reflecting mirror is disposed on the outside of the main body portion and tilted to perform positional alignment relative to the patient's eye.

Such a configuration allows the apparatus to be lightweight and compact and alignment to be performed easily and reliably ensuring a working distance.

Further features of the invention, its nature and various advantages will be more apparent from the accompanying drawings and following detailed description of the invention.

DESCRIPTION OF THE PREFERRED EMBODIMENTS

The present invention will now be described in detail with reference to the embodiments shown in the accompanying drawings.

Figure 1:
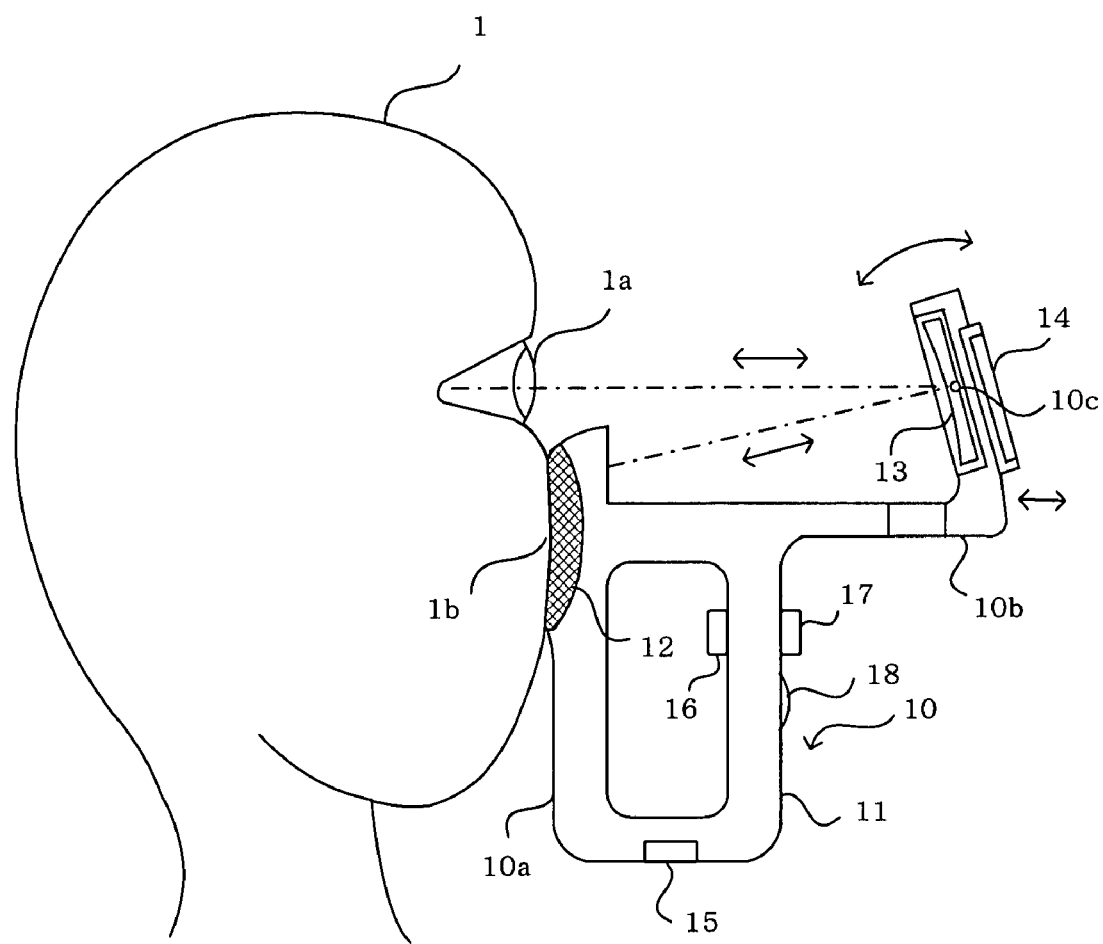
FIG. 1 is a side view showing a configuration of the hand-held ocular fundus imaging apparatus of the present invention.

FIG. 1 shows an embodiment of a hand-held ocular fundus imaging apparatus 10 (fundus camera) of the present invention. The ocular fundus imaging apparatus 10 includes a grip 11 that enables an examiner to take hold of the apparatus 10, and a face pad 12 that can be secured against a part 1b (in the vicinity below the eyelids) of the face of a patient 1 when fundus images are taken.

The grip 11 is provided with operating means such as a main switch 15, a mirror adjustment lever 16, a photographic switch 17, a focusing dial 18, and the like. The operating means are designed to be easily operated when the examiner takes hold of the grip 11 and secures the face pad 12 against the face of the patient in order to take photographs.

A main body portion 10a includes the grip 11 and the face pad 12 and the casing thereof houses optical systems such as an illumination optical system and a photographic optical system, a controller that performs control in accordance with the operation of the operating means, a drive circuit, a recording medium, and the like, as will be described later. A reflecting mirror 13 is tiltably attached to the exterior of the main body portion 10a, and a monitor 14 that allows the fundus of the patient's eye 1a to be observed is attached on the side of the reflecting mirror 13 opposite the patient.

Figure 2:
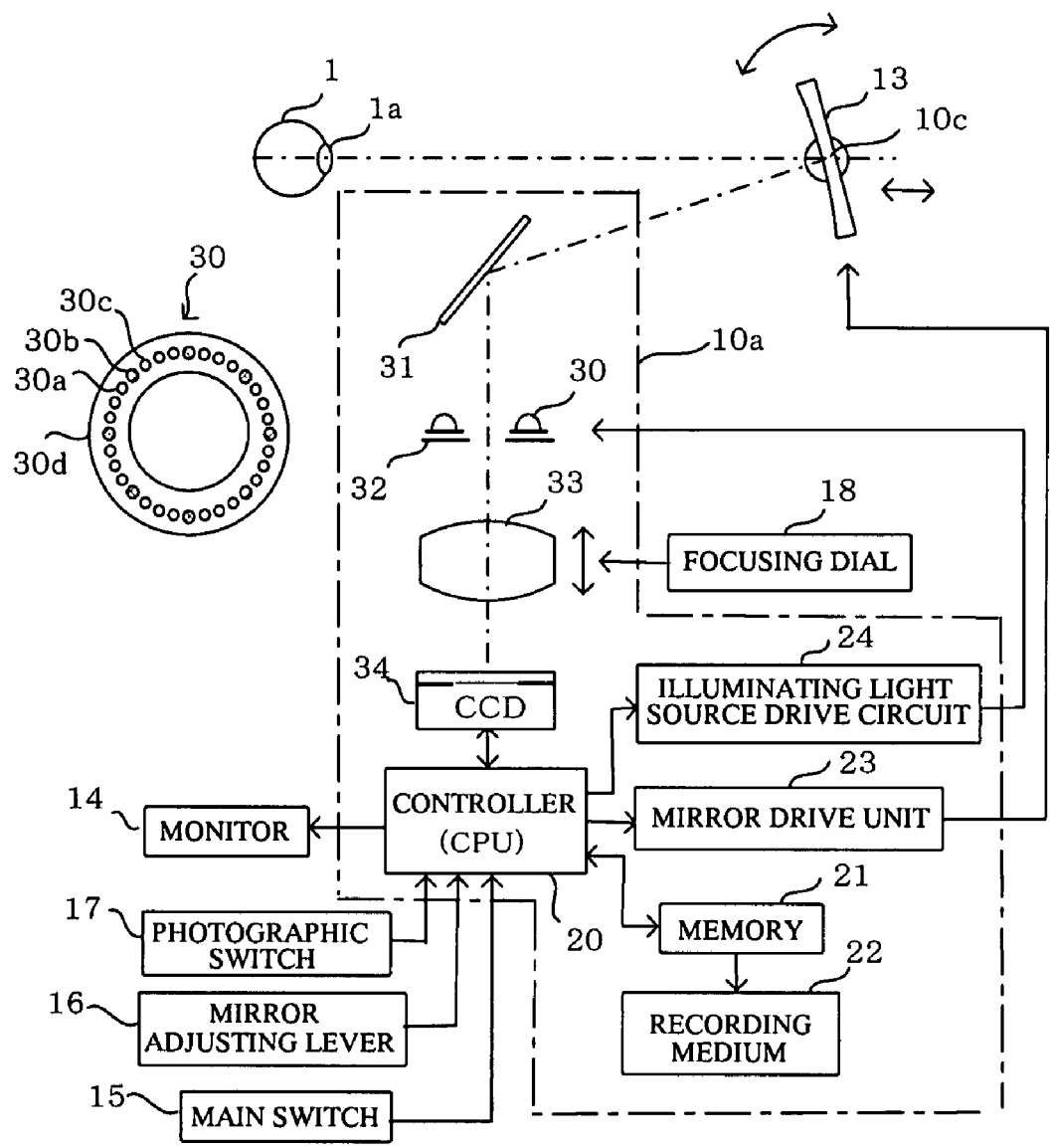
FIG. 2 is an illustrative block diagram showing the configuration of the optical system and the control system of the hand-held ocular fundus imaging apparatus.

FIG. 2 shows the configuration of the optical systems as well as the control configuration. The main body portion 10a houses an optical system composed of an illuminating light source 30, a flat mirror 31, a photographic aperture 32, and an imaging lens 33. The illuminating light source 30 is composed of a ring plate 30d on the periphery of which red light-emitting diodes 30a, green light-emitting diodes 30b, and blue light-emitting diodes 30c are disposed in a regular fashion so as to form an illuminating aperture. The light emitted from the illuminating light source 30 is reflected first by the flat mirror 31 and then by a reflecting mirror 13 formed as a concave mirror so as to correspond to an objective lens, and is directed to the patient's eye 1a. Reflected light from the fundus illuminated by the illuminating light source 30 returns to the reflecting mirror 13 and is reflected towards the flat mirror 31. This light passes through the photographic aperture 32 disposed behind the illuminating light source 30 and is directed by the imaging lens 33 onto a CCD 34 as an imaging device on which an image of the fundus is taken. The illuminating light source 30 (illuminating aperture), the flat mirror 31, and the reflecting mirror 13 constitute an illuminating optical system, and the reflecting mirror 13, the flat mirror 31, the photographic aperture 32, the imaging lens 33 and other elements constitute a photographic optical system. Since the imaging lens 33 is moved along the optical axis by a focusing dial 18 provided on the grip 11, the CCD 34 can capture a fundus image that is in focus.

The main body portion 10a is provided therein with a controller 20 composed of a CPU or the like. The controller 20 drives an illuminating light source drive circuit 24 in accordance with the turning on and off of the main switch 15, turns the illuminating light source 30 on and off, and also drives a mirror drive unit 23 to move the reflecting mirror 13 upon receiving a signal from the mirror adjustment lever 16. The reflecting mirror 13 is supported on a supporting member 10b linked to the main body portion 10a, as shown in FIG. 1. This supporting member 10b is capable of moving along the optical axis and rotating forwards and backwards around a horizontal shaft 10c that is provided to the supporting member 10b and is perpendicular to the surface of the diagram. Therefore, the reflecting mirror 13 can be moved along the optical axis and rotated around the horizontal shaft 10c by the mirror drive unit 23 to adjust the angle of the reflecting mirror 13 in relation to the patient's eye 1a as well as the position of the reflecting mirror 13.

The controller 20 either displays the fundus image captured by the CCD 34 on the observation monitor 14, or temporarily stores the fundus image captured by the CCD 34 in memory 21 and retains the image in a recording medium 22 in accordance with a signal from the photographic switch 17.

In this configuration, when the fundus of the patient's eye 1a is photographed, the examiner holds the apparatus by taking hold of the grip 11 with one hand, and presses the face pad 12 against the area 1b below the eyelids of the patient, completely securing the main body portion 10a relative to the patient. A stable positional relationship can thereby be maintained between the ocular fundus imaging apparatus 10 and the patient's eye 1a, and there is little chance of part of the apparatus coming into contact with the patient's cornea even with a short working distance.

Next, the main switch 15 is operated to turn on the illuminating light source 30, and the fundus is illuminated with illuminating light. Operating the mirror adjustment lever 16 adjusts the incline and movement of the reflecting mirror 13 along the optical axis, and thereby simultaneously moves the image of the photographic aperture 32 and the image of the illuminating aperture (illuminating light source 30), thus moving the position of the entrance pupil. Alignment is performed so that these images come into positions that are substantially conjugate with the pupil of the patient's eye 1a.

In the present invention, an optical element (reflecting mirror 13) corresponding to an objective of a fundus camera is disposed separately on the exterior of the main body portion 10a so as to be capable of moving during alignment. The alignment operation is thus performed by moving the reflecting mirror 13 while the main body portion is completely and stably secured against the area below the patient's eye. Therefore, the alignment operation is more stable and reliable than a system in which alignment is performed by moving the entire apparatus.

The alignment operation can be performed simply by inclining the reflecting mirror 13 and moving the reflecting mirror along the optical axis, or by adjusting the inclination of the flat mirror 31 and moving the reflecting mirror 13 along the optical axis. Alternatively, alignment can be performed by moving the reflecting mirror 13 in a manner perpendicular and parallel to the optical axis.

When alignment has been completed to a certain extent, the focusing dial 18 is used to bring the fundus into focus by moving the imaging lens 33 along the optical axis, and alignment is again reliably performed and completed. With the alignment complete, the photographic switch 17 is pressed. At this time, the controller 20 instantaneously increases the amount of light from the illuminating light source 30 via the illuminating light source drive circuit 24, and the fundus illuminated by this increased amount of illuminating light is captured as a still image by the CCD 34. This captured fundus image is temporarily stored in the memory 21 and is retained in the recording medium 22, which can be removed from the apparatus main body.

In the present invention, the lever 16 for moving the reflecting mirror 13, the focusing dial 18 for adjusting the focus, the photographic switch 17, and other operating devices are disposed on the grip 11 by which the examiner takes hold of the apparatus. It is therefore possible to obtain an easily operated hand-held ocular fundus camera, wherein all the operations can be performed with one hand.

In the embodiment as described above, alignment may also be performed with the arrangement of the reflecting mirror (concave mirror) 13 and the flat mirror 31 reversed, in which case the flat mirror 31 is disposed on the exterior of the main body portion 10a, and the inclination and/or position of the flat mirror 31 along the optical axis is adjusted with the aid of the lever 16.

The color and amount of light of the illuminating light source 30 can be adjusted by varying the number of colored light-emitting diodes 30a through 30c of the illuminating light source 30, the arrangement of the diodes, and the amount of light emitted from each of the light-emitting diodes.

Figure 3:
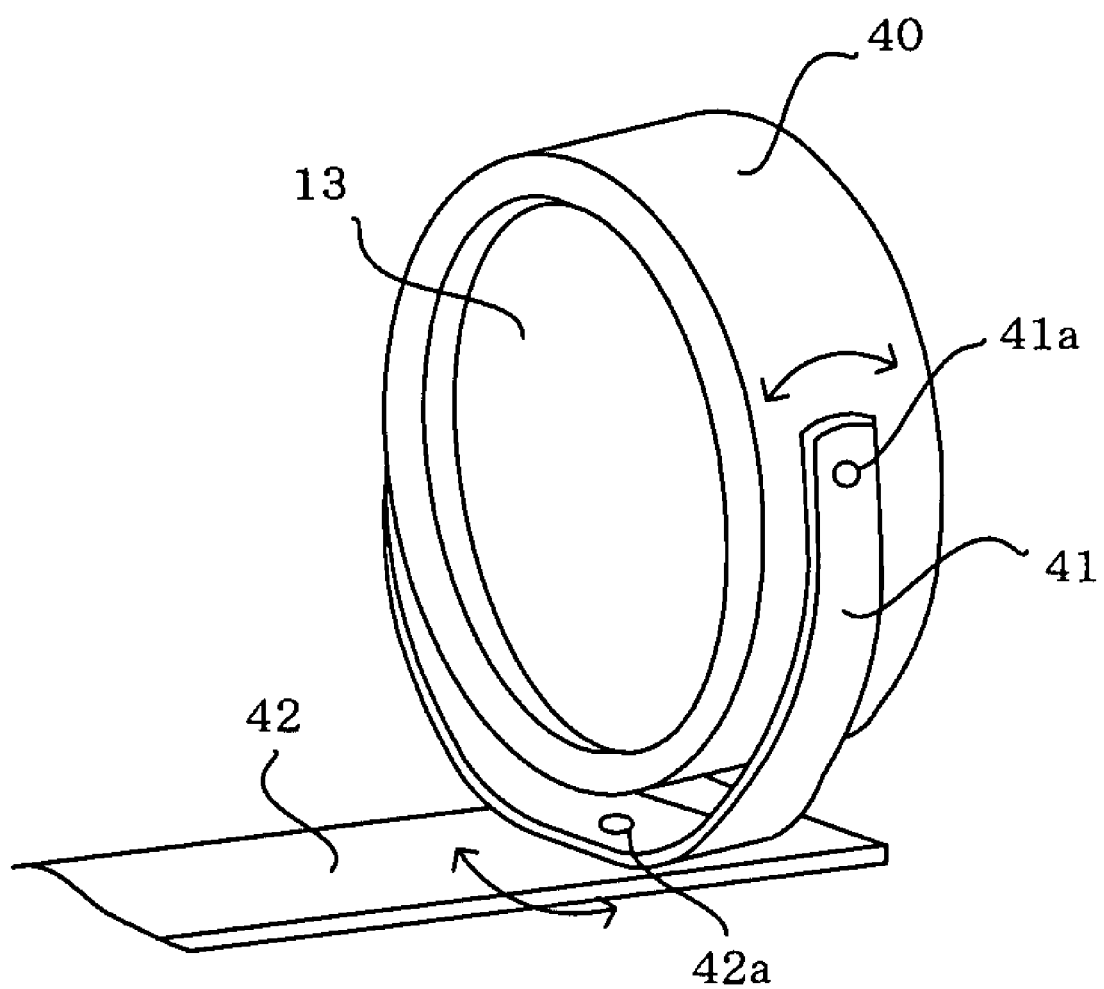
FIG. 3 is a perspective view showing the mechanism for moving the reflecting mirror in three dimensions.

As shown in FIG. 3, the reflecting mirror 13 can be moved three-dimensionally. In FIG. 3, a lens tube 40 for holding the reflecting mirror 13 is configured to be capable of rotating forwards and backwards around a horizontal pin 41a of an oscillating member 41, and also to be capable of rotating around a vertical pin 42a of a supporting part 42 that links the oscillating member 41 to the main body portion 10a. In this type of configuration, the mirror drive unit 23 causes the reflecting mirror 13 to rotate around both a horizontal and vertical axis, thereby allowing the angle of the reflecting mirror in relation to the patient's eye 1a to be adjusted three-dimensionally.

Figure 4:
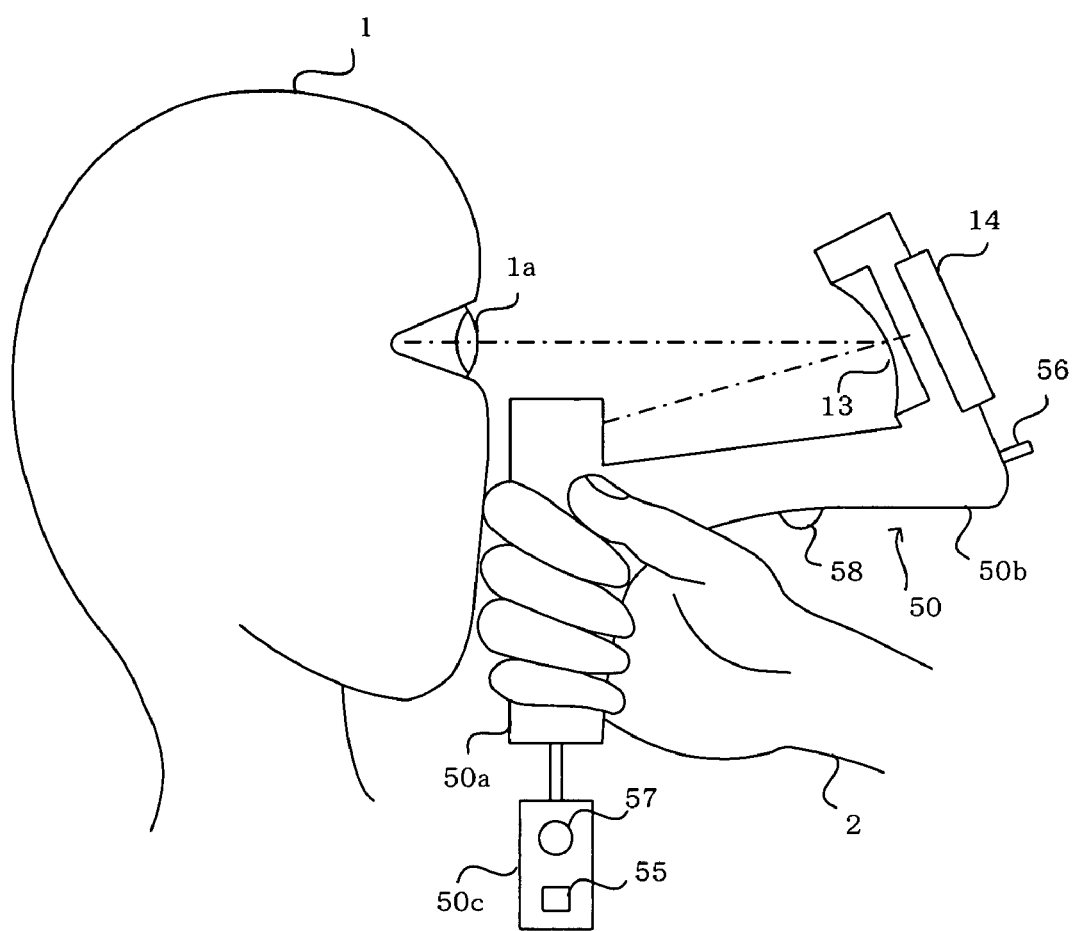
FIG. 4 is a side view showing another embodiment of the hand-held ocular fundus imaging apparatus of the present invention.

FIG. 4 shows another embodiment of a hand-held ocular fundus imaging apparatus, which is denoted by the numerical symbol 50. This hand-held ocular fundus imaging apparatus 50 has a grip 50a that the examiner holds with one hand 2, a supporting part 50b integrated with the grip 50a, and an operating unit 50c joined at the bottom of the grip 50a. The grip 50a, or the portion including the grip and the supporting part 50b, constitutes a main body portion, and this main body portion houses the optical elements 30 through 33, the CCD 34, the controller 20, the memory 21, the recording medium 22, the mirror drive unit 23, the illuminating light source drive circuit 24, and other components, all of which are shown in 10a in FIG. 2. In this optical system, the reflecting mirror 13 is attached to the exterior of the supporting part 50b, i.e., to the exterior of the main body portion, and the monitor 14 is attached to the side opposite the reflecting mirror 13.

A focusing dial 58 corresponding to the focusing dial 18 in FIG. 2 is attached underneath the supporting part 50b, and a mirror adjustment lever 56 corresponding to the mirror adjustment lever 16 in FIG. 2 is attached below the monitor 14 on the supporting part 50b. Furthermore, a main switch 55 and a photographic switch 57 that correspond to the main switch 15 and photographic switch 17, respectively, in FIG. 2 are attached to the operating unit 50c.

When the fundus of the patient's eye 1a is photographed in this type of configuration, the examiner supports the apparatus by taking hold of the grip 50a with one hand 2, and brings this hand against the area below the patient's eyelids to maintain a stable positional relationship between the ocular fundus imaging apparatus 50 and the patient's eye 1a. The operations are otherwise identical to the embodiment in FIG. 1, except that the operations are performed with the other hand (not shown).

For sanitary purposes, the inspector wears a glove on the hand 2 when the hand 2 holding the grip is supporting the apparatus while pressed against the face of the patient. Alternatively, a handkerchief may be placed between the hand 2 and the patient's face while the hand 2 is pressed against the patient's face.

Specifically, the main switch 55 is operated with the other hand to turn on the illuminating light source 30 and illuminate the fundus with illuminating light. The mirror adjustment lever 56 is then operated with the other hand to adjust the inclination and movement of the reflecting mirror 13 along the optical axis and to move the entrance pupil. Alignment is performed so that the image of the photographic aperture 32 and the image of the illuminating aperture (illuminating light source 30) are in substantially conjugate positions with the pupil of the patient's eye 1a.

When alignment has been completed to a certain extent, the focusing dial 58 is used with the other hand to bring the fundus into focus, and alignment is again reliably performed and completed. With the alignment complete, the photographic switch 57 is pressed with the other hand to photograph the fundus. This captured fundus image is temporarily stored in the memory 21 and is retained in the recording medium 22, which can be removed from the apparatus main body.

In this embodiment, since one hand 2 takes hold of the grip 50a and this hand 2 is pressed against the patient, it is possible to obtain an easily operated hand-held fundus camera similar to the embodiment in FIG. 1 because the positional relationship between the apparatus 50 and the patient's eye 1a is stable, and all of the operations can be performed with the other hand.

In the embodiment in FIG. 4, alignment may also be performed with the arrangement of the reflecting mirror 13 and the flat mirror 31 reversed, in which case the flat mirror 31 is disposed on the exterior of the main body portion, and the inclination and/or position of the flat mirror 31 along the optical axis is adjusted with the aid of the lever 56.

Also in the embodiment in FIG. 4, the reflecting mirror 13 can be moved three-dimensionally by using the configuration shown in FIG. 3.

It is also possible in the embodiment in FIG. 4 to provide the same face pad as in the embodiment in FIG. 1 to the top of the grip 50a, and to support the apparatus by securing the face pad against the patient's face. Alternatively, it is possible in the embodiment in FIG. 1 to support the apparatus by pressing the examiner's hand holding the grip against part of the patient's face, similar to the embodiment in FIG. 4. Therefore, in cases in which the face pad is provided, a more stable positional relationship between the ocular fundus imaging apparatus and the patient's eye can be maintained because the apparatus can be supported by securing the face pad against part of the patient's face as in the embodiment in FIG. 1, or by additionally pressing the examiner's hand holding the grip against part of the patient's face.

What is claimed is:

1. A hand-held ocular fundus imaging apparatus operated while a face pad or a hand holding a grip is secured against part of a patient's face, the apparatus comprising:
    a tiltable reflecting mirror for moving the position of an entrance pupil; and
    an optical system for observing and photographing a patient's eye via the reflecting mirror;
    wherein the reflecting mirror is tilted to perform positional alignment relative to the patient's eye.

2. A hand-held ocular fundus imaging apparatus according to claim 1, wherein operating means for tilting the reflecting mirror is disposed on the grip so as to be operatable by a hand holding the grip.

3. A hand-held ocular fundus imaging apparatus according to claim 1, wherein operating means for bringing the fundus of the patient's eye into focus is disposed on the grip so as to be operatable by a hand holding the grip.

4. A hand-held ocular fundus imaging apparatus according to claim 1, wherein a photographic switch for photographing still images is disposed on the grip so as to be operatable by a hand holding the grip.

5. A hand-held ocular fundus imaging apparatus according to claim 1, wherein a main switch is disposed on the grip so as to be operatable by a hand holding the grip.

6. A hand-held ocular fundus imaging apparatus according to claim 1, wherein operating means for tilting the reflecting mirror is attached so as to be operatable by a hand opposite the hand holding the grip.

7. A hand-held ocular fundus imaging apparatus according to claim 1, wherein operating means for bringing the fundus of the patient's eye into focus is attached so as to be operatable by a hand opposite the hand holding the grip.

8. A hand-held ocular fundus imaging apparatus according to claim 1, wherein a photographic switch for photographing still images is attached so as to be operatable by a hand opposite the hand holding the grip.

9. A hand-held ocular fundus imaging apparatus according to claim 1, wherein a main switch is attached so as to be operatable by a hand opposite the hand holding the grip.

10. A hand-held ocular fundus imaging apparatus according to claim 1, wherein the reflecting mirror is a concave mirror.

11. A hand-held ocular fundus imaging apparatus according to claim 1, wherein the reflecting mirror is optically disposed in front of a photographic aperture.

12. A hand-held ocular fundus imaging apparatus according to claim 1, wherein a light source for illuminating the patient's eye is configured from a plurality of light-emitting diodes.

13. A hand-held ocular fundus imaging apparatus wherein a face pad or a hand holding a grip is secured against part of a patient's face to image a fundus of a patient's eye, the apparatus comprising:
    a tiltable reflecting mirror for moving the position of an entrance pupil; and
    an optical system for observing and photographing a patient's eye via the tiltable reflecting mirror;
    wherein the optical system except for the reflecting mirror is disposed inside a main body portion containing the grip, and the reflecting mirror is disposed on the outside of the main body portion and tilted to perform positional alignment relative to the patient's eye.

14. A hand-held ocular fundus imaging apparatus according to claim 13, wherein operating means for tilting the reflecting mirror is disposed on the grip so as to be operatable by a hand holding the grip.

15. A hand-held ocular fundus imaging apparatus according to claim 13, wherein operating means for bringing the fundus of the patient's eye into focus is disposed on the grip so as to be operatable by a hand holding the grip.

16. A hand-held ocular fundus imaging apparatus according to claim 13, wherein a photographic switch for photographing still images is disposed on the grip so as to be operatable by a hand holding the grip.

17. A hand-held ocular fundus imaging apparatus according to claim 13, wherein a main switch is disposed on the grip so as to be operatable by a hand holding the grip.

18. A hand-held ocular fundus imaging apparatus according to claim 13, wherein operating means for tilting the reflecting mirror is attached so as to be operatable by a hand opposite the hand holding the grip.

19. A hand-held ocular fundus imaging apparatus according to claim 13, wherein operating means for bringing the fundus of the patient's eye into focus is attached so as to be operatable by a hand opposite the hand holding the grip.

20. A hand-held ocular fundus imaging apparatus according to claim 13, wherein a photographic switch for photographing still images is attached so as to be operatable by a hand opposite the hand holding the grip.

21. A hand-held ocular fundus imaging apparatus according to claim 13, wherein a main switch is attached so as to be operatable by a hand opposite the hand holding the grip.

22. A hand-held ocular fundus imaging apparatus according to claim 13, wherein the reflecting mirror is a concave mirror.

23. A hand-held ocular fundus imaging apparatus according to claim 13, wherein the reflecting mirror is optically disposed in front of a photographic aperture.

24. A hand-held ocular fundus imaging apparatus according to claim 13, wherein a light source for illuminating the patient's eye is configured from a plurality of light-emitting diodes.

* * * * *